US012661142B2

(12) United States Patent
Barnes et al.

(10) Patent No.: US 12,661,142 B2
(45) Date of Patent: *Jun. 23, 2026

(54) OSCILLATING SURGICAL BONE REMOVAL TOOL WITH ANGULAR DISPLACEMENT

(71) Applicant: Medtronic PS Medical, Inc., Goleta, CA (US)

(72) Inventors: Milton F. Barnes, Grand Prairie, TX (US); Michael Vu, Grand Prairie, TX (US)

(73) Assignee: Medtronic PS Medical, Inc., Goleta, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 18/511,080

(22) Filed: Nov. 16, 2023

(65) Prior Publication Data

US 2024/0156486 A1     May 16, 2024

Related U.S. Application Data

(60) Provisional application No. 63/425,856, filed on Nov. 16, 2022.

(51) Int. Cl.
A61B 17/32          (2006.01)
(52) U.S. Cl.
CPC ................ *A61B 17/320092* (2013.01); *A61B 17/32002* (2013.01); *A61B 2017/320069* (2017.08);
(Continued)
(58) Field of Classification Search
CPC ...... A61B 17/320092; A61B 17/32002; A61B 2017/320069; A61B 2017/320071; A61B 2017/320072; A61B 17/1624
See application file for complete search history.

(56) References Cited

U.S. PATENT DOCUMENTS

| 233,709 | A | 10/1880 | Starr |
| 288,676 | A | 11/1883 | Stearns |
| | | (Continued) | |

FOREIGN PATENT DOCUMENTS

| CH | 686113 A5 | 1/1996 |
| CN | 1150073 A | 5/1997 |
| | (Continued) | |

OTHER PUBLICATIONS

International Search Report PCT/US2023/080139 dated Apr. 23, 2024, 19pp.
(Continued)

*Primary Examiner* — Ashley L Fishback
(74) *Attorney, Agent, or Firm* — Carter, DeLuca & Farrell LLP

(57)          ABSTRACT

A surgical device for cutting or shaving bone or tissue includes a housing having an elongated tube extending therefrom, the elongated tube configured to support a surgical tool at a distal end thereof. A gear assembly is disposed within the housing and is configured to control oscillation of the surgical tool. A motor is operably coupled to the housing and is configured to drive the gear assembly upon activation thereof. The motor is moveable relative to the housing to adjust one or more gears of the gear assembly which, in turn, adjusts an oscillation angle of the surgical tool to control the aggressiveness of the surgical tool when cutting tissue or bone.

20 Claims, 7 Drawing Sheets

(52) U.S. Cl.
CPC ............. *A61B 2017/320071* (2017.08); *A61B 2017/320072* (2013.01)

(56) References Cited

U.S. PATENT DOCUMENTS

| | | | |
|---|---|---|---|
| 1,043,098 | A | 11/1912 | Gross |
| 1,053,709 | A | 2/1913 | Collins |
| 1,112,349 | A | 9/1914 | Barnes |
| 1,209,362 | A | 12/1916 | Turner |
| 1,539,439 | A | 5/1925 | Oscar |
| 1,862,337 | A | 6/1932 | Emrick |
| 2,477,058 | A | 7/1949 | Harborne et al. |
| 2,512,033 | A | 6/1950 | Metz |
| 2,522,388 | A | 9/1950 | Madsen |
| 2,596,594 | A | 5/1952 | Petre |
| 2,682,184 | A | 6/1954 | Szarkowski |
| 2,726,872 | A | 12/1955 | Onsrud |
| 2,766,791 | A | 10/1956 | Givens |
| 2,773,693 | A | 12/1956 | Chittenden |
| 3,043,634 | A | 7/1962 | Samuel |
| 3,136,347 | A | 6/1964 | Linquist |
| 3,589,826 | A | 6/1971 | Fenn |
| 3,637,225 | A | 1/1972 | Schmuck |
| 3,835,858 | A | 9/1974 | Hagen |
| 3,943,986 | A | 3/1976 | Lejdegard |
| 4,035,100 | A | 7/1977 | Kruger et al. |
| 4,047,722 | A | 9/1977 | Nielsen et al. |
| 4,078,593 | A | 3/1978 | Benitz |
| 4,107,949 | A | 8/1978 | Wanner et al. |
| 4,123,074 | A | 10/1978 | Wanner |
| 4,146,240 | A | 3/1979 | Nielsen |
| 4,185,383 | A | 1/1980 | Heimke et al. |
| 4,378,053 | A | 3/1983 | Simpson |
| 4,502,734 | A | 3/1985 | Allan |
| 4,512,692 | A | 4/1985 | Nielsen |
| 4,565,472 | A | 1/1986 | Brennsteiner et al. |
| 4,594,036 | A | 6/1986 | Hogenhout |
| 4,655,651 | A | 4/1987 | Hunger et al. |
| 4,823,468 | A | 4/1989 | Kollegger |
| 4,830,000 | A | 5/1989 | Shutt |
| 4,917,274 | A | 4/1990 | Asa et al. |
| 5,009,440 | A | 4/1991 | Manschitz |
| 5,116,353 | A | 5/1992 | Green |
| 5,203,654 | A | 4/1993 | Henderson |
| 5,256,147 | A | 10/1993 | Vidal et al. |
| 5,263,786 | A | 11/1993 | Kageyama |
| 5,286,145 | A | 2/1994 | Kleine |
| 5,352,234 | A | 10/1994 | Scott |
| 5,382,249 | A | 1/1995 | Fletcher |
| 5,421,682 | A | 6/1995 | Obermeier et al. |
| 5,439,005 | A | 8/1995 | Vaughn |
| 5,466,101 | A | 11/1995 | Meyen |
| 5,487,626 | A | 1/1996 | Von Holst et al. |
| 5,499,985 | A | 3/1996 | Hein et al. |
| 5,505,737 | A | 4/1996 | Gosselin et al. |
| 5,549,634 | A | 8/1996 | Scott et al. |
| 5,569,256 | A | 10/1996 | Vaughn et al. |
| D377,982 | S | 2/1997 | Walen |
| 5,601,560 | A | 2/1997 | Del Rio et al. |
| 5,634,933 | A | 6/1997 | McCombs et al. |
| 5,697,158 | A | 12/1997 | Klinzing et al. |
| 5,720,749 | A | 2/1998 | Rupp |
| 5,735,535 | A | 4/1998 | McCombs et al. |
| 5,741,263 | A | 4/1998 | Umber et al. |
| 5,782,836 | A | 7/1998 | Umber et al. |
| 5,807,040 | A | 9/1998 | Bongers-Ambrosius et al. |
| 5,810,802 | A | 9/1998 | Panescu et al. |
| 5,833,704 | A | 11/1998 | McCombs et al. |
| 5,851,094 | A | 12/1998 | Strand et al. |
| 5,888,200 | A | 3/1999 | Walen |
| 5,893,851 | A | 4/1999 | Umber et al. |
| 5,928,241 | A | 7/1999 | Menut et al. |
| 5,941,891 | A | 8/1999 | Walen |
| 5,964,555 | A | 10/1999 | Strand |
| 5,989,257 | A | 11/1999 | Tidwell et al. |
| 6,000,940 | A | 12/1999 | Buss et al. |
| 6,007,541 | A | 12/1999 | Scott |
| 6,033,408 | A | 3/2000 | Gage et al. |
| 6,062,575 | A | 5/2000 | Mickel et al. |
| 6,209,886 | B1 | 4/2001 | Estes et al. |
| 6,261,035 | B1 | 7/2001 | Moores, Jr. et al. |
| 6,267,763 | B1 | 7/2001 | Castro |
| RE37,358 | E | 9/2001 | Del Rio et al. |
| 6,290,525 | B1 | 9/2001 | Jacobi |
| 6,409,221 | B1 | 6/2002 | Robinson et al. |
| 6,447,484 | B1 | 9/2002 | Briscoe et al. |
| 6,607,533 | B2 | 8/2003 | Del Rio et al. |
| 6,612,588 | B2 | 9/2003 | Ostermeier et al. |
| 6,688,610 | B2 | 2/2004 | Huggins et al. |
| 6,723,101 | B2 | 4/2004 | Fletcher et al. |
| 6,733,218 | B2 | 5/2004 | Del Rio et al. |
| D492,412 | S | 6/2004 | Desoutter et al. |
| 6,746,153 | B2 | 6/2004 | Del Rio et al. |
| 6,780,189 | B2 | 8/2004 | Tidwell et al. |
| 6,811,190 | B1 | 11/2004 | Ray et al. |
| 6,976,815 | B2 | 12/2005 | Berglow et al. |
| 7,001,391 | B2 | 2/2006 | Estes et al. |
| 7,011,661 | B2 | 3/2006 | Riedel et al. |
| 7,066,940 | B2 | 6/2006 | Riedel et al. |
| D536,791 | S | 2/2007 | Eskridge et al. |
| 7,261,169 | B2 | 8/2007 | Kleine et al. |
| 7,374,375 | B2 | 5/2008 | Kleine et al. |
| 7,429,154 | B2 | 9/2008 | Kleine et al. |
| 7,465,309 | B2 | 12/2008 | Walen |
| 7,488,327 | B2 | 2/2009 | Rathbun et al. |
| 7,497,860 | B2 | 3/2009 | Carusillo et al. |
| 7,549,992 | B2 | 6/2009 | Shores et al. |
| 7,559,927 | B2 | 7/2009 | Shores et al. |
| D609,810 | S | 2/2010 | Cote et al. |
| 7,669,308 | B2 | 3/2010 | Oshnock et al. |
| 7,691,106 | B2 | 4/2010 | Schenberger et al. |
| 7,722,054 | B2 | 5/2010 | Young |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| 7,766,585 | B2 | 8/2010 | Vasudeva et al. |
| D631,962 | S | 2/2011 | Dorman |
| D636,082 | S | 4/2011 | Cote et al. |
| 7,922,720 | B2 | 4/2011 | May et al. |
| D641,468 | S | 7/2011 | Ruiz, Sr. et al. |
| 8,043,292 | B2 | 10/2011 | Carusillo |
| D648,021 | S | 11/2011 | Dorman |
| D666,294 | S | 8/2012 | Miles et al. |
| 8,361,068 | B2 | 1/2013 | McClurken |
| 8,419,760 | B2 | 4/2013 | Wiebe, III |
| 8,518,065 | B2 | 8/2013 | Shores |
| D692,134 | S | 10/2013 | Lee-Sepsick |
| 8,597,316 | B2 | 12/2013 | McCombs |
| 8,702,710 | B2 | 4/2014 | Carusillo |
| 8,801,713 | B2 | 8/2014 | del Rio et al. |
| 8,893,820 | B2 | 11/2014 | Barhitte et al. |
| D728,098 | S | 4/2015 | Schad et al. |
| D728,099 | S | 4/2015 | Schad et al. |
| D744,650 | S | 12/2015 | Catron et al. |
| D746,457 | S | 12/2015 | Swick et al. |
| D747,477 | S | 1/2016 | Freigang et al. |
| D753,826 | S | 4/2016 | Eggeling et al. |
| 9,333,561 | B2 | 5/2016 | Nakai et al. |
| 9,597,737 | B2 | 3/2017 | Hecht |
| 10,080,579 | B2 | 9/2018 | Cihak et al. |
| 10,314,610 | B2 | 6/2019 | Dexter et al. |
| 10,588,640 | B2 | 3/2020 | Steinhauser et al. |
| 11,154,319 | B2 | 10/2021 | Dexter et al. |
| 2002/0105149 | A1 | 8/2002 | Karst |
| 2002/0151902 | A1 | 10/2002 | Riedel et al. |
| 2002/0171208 | A1 | 11/2002 | Lechot et al. |
| 2003/0060841 | A1 | 3/2003 | Del Rio et al. |
| 2003/0097133 | A1 | 5/2003 | Green et al. |
| 2003/0130663 | A1 | 7/2003 | Walen |
| 2003/0140743 | A1 | 7/2003 | Ofentavsek |
| 2003/0163134 | A1 | 8/2003 | Riedel et al. |
| 2003/0229351 | A1 | 12/2003 | Tidwell et al. |
| 2005/0027282 | A1 | 2/2005 | Schweikert et al. |

(56) References Cited

U.S. PATENT DOCUMENTS

| | | |
|---|---|---|
| 2005/0072007 A1 | 4/2005 | Proulx |
| 2005/0232715 A1 | 10/2005 | Baumann et al. |
| 2006/0053974 A1 | 3/2006 | Blust |
| 2007/0172321 A1 | 7/2007 | Nagai |
| 2007/0282329 A1 | 12/2007 | Kawano |
| 2008/0033280 A1 | 2/2008 | Lubock et al. |
| 2009/0024129 A1 | 1/2009 | Gordon et al. |
| 2009/0312779 A1 | 12/2009 | Boykin et al. |
| 2010/0063524 A1 | 3/2010 | McCombs |
| 2010/0076477 A1 | 3/2010 | Jezierski et al. |
| 2011/0022069 A1 | 1/2011 | Mitusina |
| 2011/0190803 A1 | 8/2011 | To et al. |
| 2011/0218562 A1 | 9/2011 | Viola et al. |
| 2011/0238070 A1 | 9/2011 | Santangelo et al. |
| 2011/0270293 A1 | 11/2011 | Malla et al. |
| 2011/0270294 A1 | 11/2011 | Rubin |
| 2012/0070220 A1 | 3/2012 | Ruiz, Sr. et al. |
| 2012/0259336 A1 | 10/2012 | del Rio et al. |
| 2012/0259337 A1 | 10/2012 | del Rio |
| 2013/0110147 A1 | 5/2013 | Dame |
| 2013/0116659 A1 | 5/2013 | Porter |
| 2013/0138096 A1 | 5/2013 | Benn |
| 2013/0144267 A1 | 6/2013 | Chan et al. |
| 2013/0245704 A1 | 9/2013 | Koltz et al. |
| 2013/0296848 A1 | 11/2013 | Allen, IV et al. |
| 2013/0304069 A1 | 11/2013 | Bono et al. |
| 2014/0056656 A1 | 2/2014 | Bae et al. |
| 2014/0124231 A1 | 5/2014 | Hessenberger et al. |
| 2014/0163558 A1 | 6/2014 | Cosgrove et al. |
| 2014/0262408 A1 | 9/2014 | Woodard |
| 2014/0303624 A1 | 10/2014 | del Rio et al. |
| 2014/0336654 A1 | 11/2014 | Pilgeram |
| 2014/0343454 A1 | 11/2014 | Miller et al. |
| 2014/0350561 A1 | 11/2014 | Dacosta et al. |
| 2014/0371752 A1 | 12/2014 | Anderson |
| 2016/0278802 A1 | 9/2016 | Cihak et al. |
| 2018/0140308 A1 | 5/2018 | Anderson |
| 2018/0185052 A1 | 7/2018 | Zhou et al. |
| 2019/0388115 A1 | 12/2019 | Nguyen |
| 2022/0338895 A1 | 10/2022 | Bono et al. |

FOREIGN PATENT DOCUMENTS

| | | | |
|---|---|---|---|
| CN | 103447599 A | 12/2013 | |
| CN | 103458805 A | 12/2013 | |
| DE | 88152618 | 3/1989 | |
| DE | 102012101259 A1 | 8/2013 | |
| EP | 0293327 A2 | 11/1988 | |
| EP | 0216354 B1 | 7/1991 | |
| EP | 1101459 B1 | 2/2006 | |
| EP | 1289714 B1 | 8/2008 | |
| EP | 1514034 B1 | 10/2011 | |
| FR | 1330849 A | 6/1963 | |
| GB | 2129730 A | 5/1984 | |
| JP | 2014516611 A | 7/2014 | |
| RU | 2077275 C1 | 4/1997 | |
| WO | 9608343 A1 | 3/1996 | |
| WO | 0166024 A1 | 9/2001 | |
| WO | 0189769 A1 | 11/2001 | |
| WO | WO-2006007590 A2 * | 1/2006 | ......... A61B 17/3472 |
| WO | 2012138337 A1 | 10/2012 | |
| WO | 2014037134 A1 | 3/2014 | |
| WO | 2014176060 A1 | 10/2014 | |

OTHER PUBLICATIONS

International Search Report and Written Opinion for International Application No. PCT/US2016/018686 dated Jul. 12, 2016 (4 pgs).
International Search Report PCT/US2023/080169, dated Mar. 4, 2024, 12pp.

* cited by examiner

OSCILLATING SURGICAL BONE REMOVAL TOOL WITH ANGULAR DISPLACEMENT

CROSS REFERENCE TO RELATED APPLICATION

This application claims the benefit of and priority to U.S. Provisional Patent Application No. 63/425,856, filed Nov. 16, 2022, the entire contents of which are hereby incorporated herein by reference.

FIELD

The present disclosure is generally directed to devices and systems for cutting and treating bone and hard tissue and biomaterials. The devices and systems of the present disclosure may be particularly suitable for orthopedical applications and other surgical procedures requiring bone removal.

BACKGROUND

Devices and systems in accordance with the present disclosure may be suitable for a variety of procedures including orthopedical surgical procedures, spinal procedures, cranial procedures, and other procedures requiring bone or hard tissue removal. During a given procedure, a motor is used to power a drill disposed at a distal end of the surgical tool. Typically, the tool is rotated at a very high RPM which allows the drill dissecting tip of the tool to plunge into the bone or, in some instances, cut or shave the bone using one or more flutes on the drill dissecting tip. However, in some instances, the rotating drill tip if improperly handled can catch adjacent tissue, cause adjacent tissue to wrap around the drill tip when a surgeon is trying to steer clear of delicate tissue, nerves, and ligaments and incidental contact with the drill tip.

One solution has been to manufacture surgical bone cutting/dissecting tools that use a drill bit and motor that employs an oscillatory motion to cut bone and hard tissue. By oscillating the drill bit, tissue is less prone to catch and wrap around the drill bit if the drill bit contacts tissue.

SUMMARY

Provided in accordance with the present disclosure is a surgical device for cutting or shaving bone or hard tissue which includes a housing having an elongated tube extending therefrom, the elongated tube configured to support a surgical tool at a distal end thereof. A gear assembly is disposed within the housing and is configured to control oscillation of the surgical tool. A motor is operably coupled to the housing and is configured to drive the gear assembly upon activation thereof. The motor is moveable relative to the housing to adjust one or more gears of the gear assembly which, in turn, adjusts an oscillation angle of the surgical tool to control the aggressiveness of the surgical tool when cutting tissue or bone.

In aspects according to the present disclosure, the motor is rotatable relative to the housing to adjust the at least one gear of the gear assembly. In other aspects according to the present disclosure, the housing includes an angular displacement mechanism which, upon actuation, is configured to allow selective rotation of the motor relative to the housing.

In aspects according to the present disclosure, movement of the motor relative to the housing effects an oscillation angle of a swing gear of the gear assembly which, in turn, effects the oscillation angle of the surgical tool.

In aspects according to the present disclosure, the surgical tool includes a drive rod that is selectively engageable within the housing. In other aspects according to the present disclosure, the drive rod of the surgical tool is selectively engageable with a collet disposed within the housing and wherein the collet is operably engageable with the gear assembly.

In aspects according to the present disclosure, the collet cooperates with a lock collar to selectively lock the drive rod of the surgical tool therein.

In aspects according to the present disclosure, the surgical tool is a drill bit configured to cut or shave bone or tissue upon activation thereof. In other aspects according to the present disclosure, the drill bit is configured to both plunge-cut into bone or tissue and side cut to shave bone or tissue.

Provided in accordance with the present disclosure is a surgical device for cutting or shaving bone or hard tissue which includes a housing having an elongated tube extending therefrom, the elongated tube configured to support a surgical tool at a distal end thereof, the surgical tool including a drive rod selectively engageable within the housing. A gear assembly is disposed within the housing and is configured to control oscillation of the surgical tool. A motor is operably coupled to the housing and is configured to drive the gear assembly upon activation thereof. A collet is disposed within the housing and is configured to selectively lock the drive rod of the surgical tool within the housing. The collet is operably engageable with the gear assembly such that actuation of the motor oscillates the surgical tool.

In aspects according to the present disclosure, the motor is rotatable relative to the housing to adjust at least one gear of the gear assembly which, in turn, adjusts an oscillation angle of the surgical tool.

In aspects according to the present disclosure, the housing includes an angular displacement mechanism which, upon actuation, is configured to allow selective rotation of the motor relative to the housing. In other aspects according to the present disclosure, rotation of the motor relative to the housing effects an oscillation angle of a swing gear of the gear assembly which, in turn, effects the oscillation angle of the surgical tool. In yet other aspects according to the present disclosure, the collet is selectively moveable within the housing to control a length of exposure of a tip of the surgical tool relative to a distal end of the elongated tube.

In aspects according to the present disclosure, the housing includes a dial disposed thereon that is rotatable relative thereto to control the length of exposure of the tip of the surgical tool relative to the distal end of the elongated tube.

Provided in accordance with the present disclosure is a surgical device for cutting or shaving bone or hard tissue which includes a housing having an elongated tube extending therefrom, the elongated tube configured to support a surgical tool at a distal end thereof, the surgical tool including a drive rod selectively engageable within the housing. A gear assembly is disposed within the housing and is configured to control oscillation of the surgical tool. A motor is operably coupled to the housing and is configured to drive the gear assembly upon activation thereof, the motor moveable relative to the housing to adjust one or more gears of the gear assembly which, in turn, adjusts an oscillation angle of the surgical tool. A collet is disposed within the housing and is configured to selectively lock the drive rod of the surgical tool within the housing. The collet is operably engageable with the gear assembly such that actuation of the motor oscillates the surgical tool, wherein the collet is selectively moveable within the housing to control a length of exposure of a tip of the surgical tool relative to a distal end of the elongated tube.

In aspects according to the present disclosure, the housing includes an angular displacement mechanism which, upon actuation, is configured to allow selective rotation of the motor relative to the housing.

In aspects according to the present disclosure, movement of the motor relative to the housing effects an oscillation angle of a swing gear of the gear assembly which, in turn, effects the oscillation angle of the surgical tool. In other aspects according to the present disclosure, movement of the motor relative to the housing moves an axis of rotation of the motor relative to an axis of rotation of the swing gear which effects the movement of a corresponding link operably connected to the swing gear which, in turn, effects the oscillation angle of the swing gear and the oscillation angle of the surgical tool.

Provided in accordance with the present disclosure is a surgical device for cutting or shaving bone or tissue which includes a housing having an elongated tube extending therefrom, the elongated tube configured to support a surgical tool at a distal end thereof, the surgical tool including an elongated drive rod operably coupled to a gear assembly disposed within the housing. A tool head includes a first pair of cutting flutes disposed on opposing sides thereof and converging to form a cutting tip at a distal end of the tool head, each flute of the first pair of flutes including cutting edges on the sides thereof that extend distally to form the cutting tip. The tool head also includes a second pair of cutting flutes disposed on opposing sides thereof, each flute of the second pair of flutes disposed between the first pair of cutting flutes and each flute of the second pair of flutes including cutting edges on the sides thereof. A motor is operably coupled to the housing and is configured to drive the gear assembly upon activation thereof to control oscillation of the elongated drive rod and the tool head.

In aspects according to the present disclosure, the second pair of cutting flutes is spaced proximally relative to the cutting tip.

In aspects according to the present disclosure, the first pair of cutting flutes is configured to facilitate plunge-cutting.

In aspects according to the present disclosure, the second pair of cutting flutes is configured to facilitate side cutting or shaving.

In aspects according to the present disclosure, the motor is moveable relative to the housing to adjust one or more gears of the gear assembly which, in turn, adjusts an oscillation angle of the surgical tool.

In aspects according to the present disclosure, the motor is moveable relative to the housing to a first position that adjusts one or more gears of the gear assembly which, in turn, adjusts an oscillation angle of the surgical tool to facilitate plunge-cutting.

In aspects according to the present disclosure, the motor is moveable relative to the housing to a second position that adjusts the position of one or more gears of the gear assembly which, in turn, adjusts an oscillation angle of the surgical tool to facilitate side cutting or shaving.

In aspects according to the present disclosure, the one or more gears is an output gear of the motor.

Provided in accordance with the present disclosure is a surgical device for cutting or shaving bone or tissue which includes a housing having an elongated tube extending therefrom, the elongated tube configured to support a surgical tool at a distal end thereof. The surgical tool includes an elongated drive rod operably coupled to a gear assembly disposed within the housing. A tool head is also included having a first pair of cutting flutes disposed on opposing sides thereof and converging to form a cutting tip at a distal end of the tool head, each flute of the first pair of flutes including cutting edges on the sides thereof that extend distally to form the cutting tip. The tool head also includes a second pair of cutting flutes disposed on opposing sides thereof, each flute of the second pair of flutes disposed between the first pair of cutting flutes and each flute of the second pair of flutes including cutting edges on the sides thereof.

A motor is operably coupled to the housing and is configured to drive the gear assembly upon activation thereof to control oscillation of the elongated drive rod and the tool head. The motor is moveable relative to the housing to adjust one or more gears of the gear assembly which, in turn, adjusts an oscillation angle of the elongated drive rod and the tool head. A collet is disposed within the housing and is configured to selectively lock the elongated drive rod of the surgical tool within the housing.

In aspects according to the present disclosure, the collet is operably engageable with the gear assembly such that actuation of the motor oscillates the surgical tool.

In aspects according to the present disclosure, the collet is selectively moveable within the housing to control a length of exposure of the tool head of the surgical tool relative to a distal end of the elongated tube.

In aspects according to the present disclosure, the elongated drive rod includes a keyed interface at a proximal end thereof to facilitate engagement with the collet.

Provided in accordance with the present disclosure is a surgical tool for cutting or shaving bone or tissue which includes an elongated drive rod configured for selective engagement within a housing of a surgical device. The tool also includes a tool head having a first pair of cutting flutes disposed on opposing sides thereof and converging to form a cutting tip at a distal end of the tool head, each flute of the first pair of flutes including cutting edges on the sides thereof that extend distally to form the cutting tip. The tool head also includes a second pair of cutting flutes disposed on opposing sides thereof, each flute of the second pair of flutes disposed between the first pair of cutting flutes and each flute of the second pair of flutes including cutting edges on the sides thereof.

In aspects according to the present disclosure, the second pair of cutting flutes is spaced proximally relative to the cutting tip.

In aspects according to the present disclosure, the first pair of cutting flutes is configured to facilitate plunge-cutting.

In aspects according to the present disclosure, the second pair of cutting flutes is configured to facilitate side cutting or shaving.

BRIEF DESCRIPTION OF THE DRAWINGS

In the drawings, where like numerals refer to like components throughout several views.

DETAILED DESCRIPTION

Figure 1:
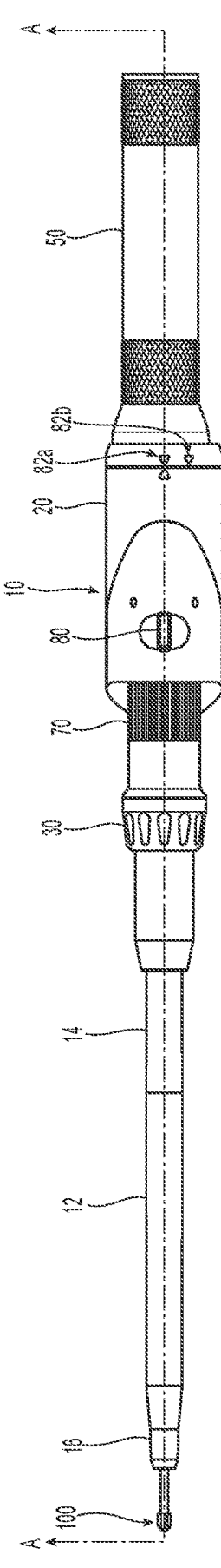
FIG. 1 is a top view of a cutting and shaving surgical device according to one embodiment of the present disclosure.
Figure 2:
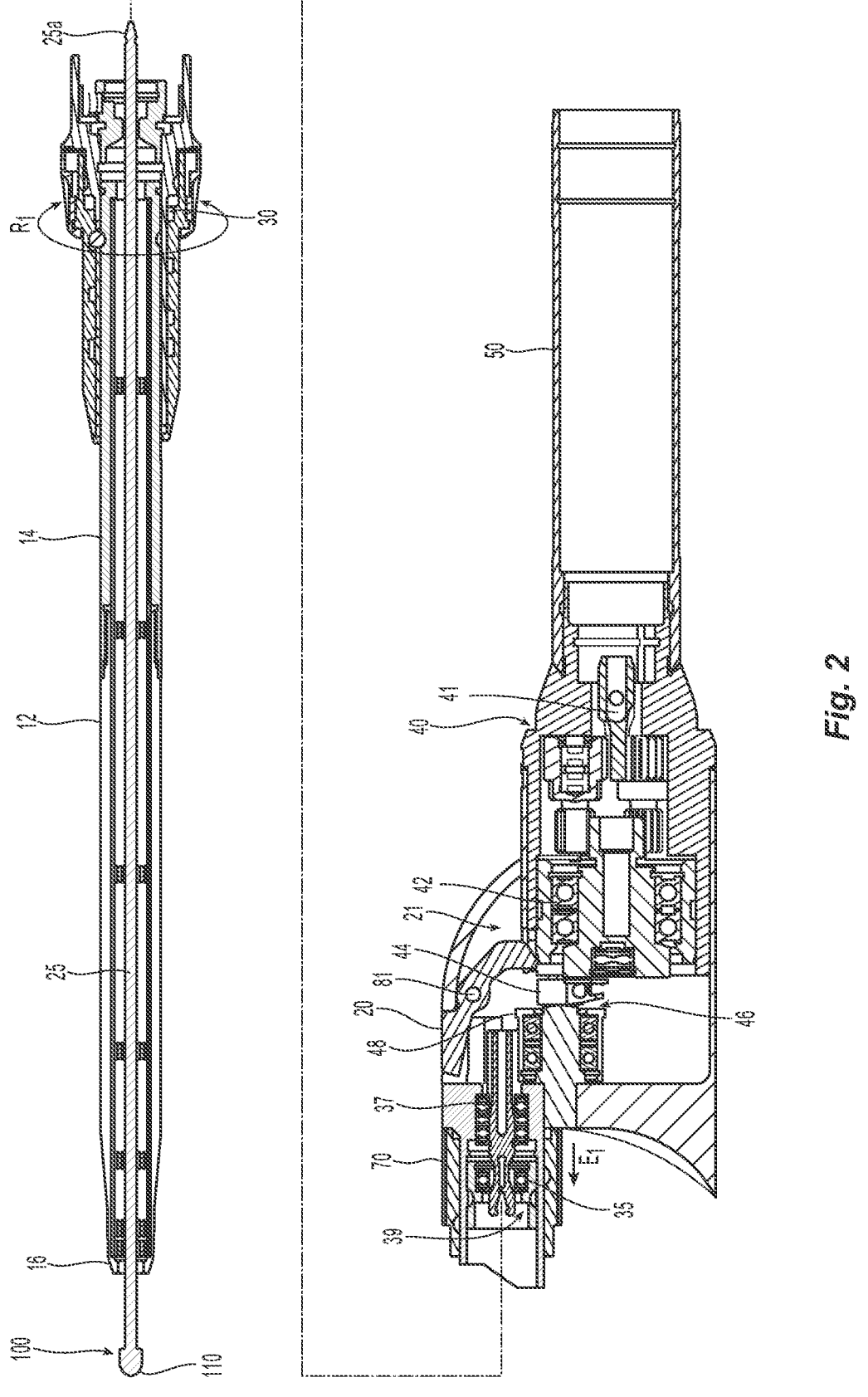
FIG. 2 is a side, cross sectional view of the cutting and shaving surgical device of FIG. 1 taken along line A-A of FIG. 1 showing a gear assembly disposed therein.
Figure 3:
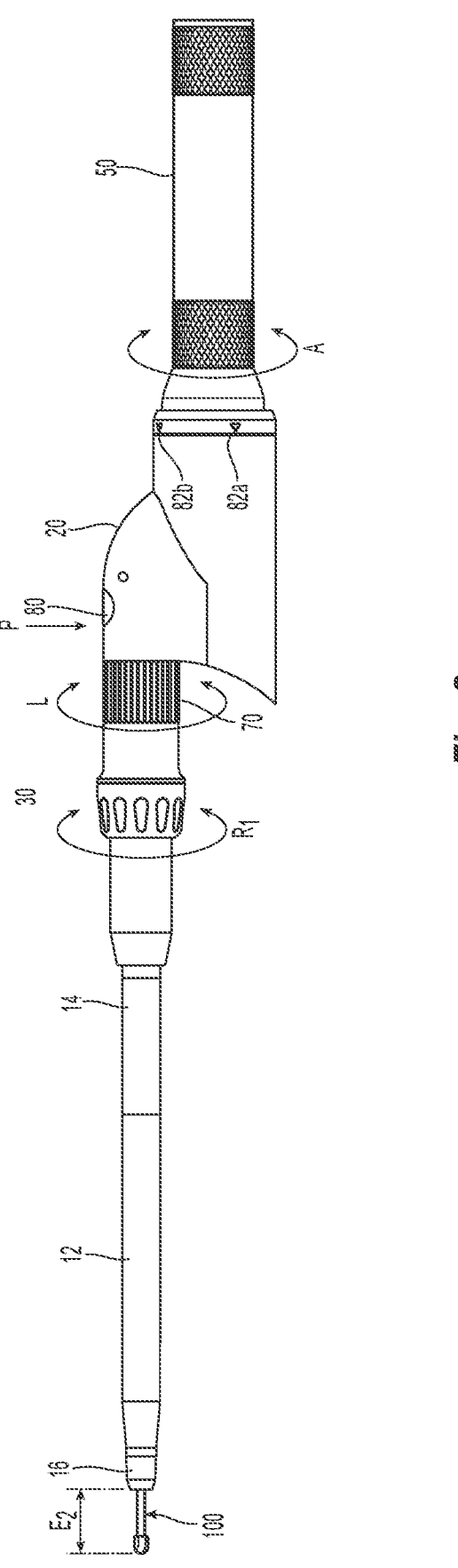
FIG. 3 is a side view of the cutting and shaving surgical device of FIG. 1.

FIGS. 1-3 illustrate one embodiment of a surgical device 10 configured for use in orthopedic and cranial surgical procedures for dissecting, cutting, shaving, and otherwise removing bone and hard tissue. Device 10 includes a housing 20 configured to be handled by a surgeon having a motor 50 operably associated therewith. Motor 50 may be ultimately connected to power source (not shown) or configured to house a battery (not shown) for portable use. Motor 50 is configured to operate at various speeds that may be controlled by a user via a speed dial or switch on the housing 20 or may be controlled at the power source. An elongated tube 12 extends from a distal end of the housing 20 and is configured to support a surgical tool 100, e.g., drill bit, dissecting head or bone shaver, at a distal end 16 thereof. A proximal end 14 of the tube 12 is removably engageable with the housing 20 and is lockable therein via a locking collet 70, a description of which is provided below. Elongated tube 12 may be configured to support the surgical tool 100 atop bearings (not shown) spaced therealong.

Housing 20 includes a cavity 21 defined therein configured to house a gear assembly 40 that operably engages the motor 50. More particularly, gear assembly 40 includes an input shaft 41 that is configured to operably engage a motor rotor shaft or collet (not shown) of the motor 50 (FIG. 2) such that rotational output of the rotor shaft correspondingly rotates the input shaft 41 at a 1:1 ratio. In embodiments, other gear ratios are contemplated. Input shaft 41 connects to a series of gears disposed within the housing 20 that cooperate to rotate a gear output shaft 42 at a desired speed (rotations per minute or RPM). Moreover, in certain integral systems, the rotor shaft of the motor 50 may be common and be the input gear 41 of the gear assembly 40.

The gear output shaft 42 couples to a link 44 that drives swing gear 48 such that the rotational output of the output shaft 42 is converted into oscillatory motion of the swing gear 48. The swing gear 48, in turn, couples to an oscillation converter 46 (which may include any known type of oscillation converter mechanism) that ultimately connect to a tool shaft 25 of the surgical tool at a proximal end thereof. Generally, the oscillation converter 46 is a subassembly of components that convert the rotary motion of the output gear 42 to oscillatory motion to move the tool shaft 25. In this instance, the subassembly of components includes the output gear 42, link 44, swing gear 48 and tool driveshaft 37.

The gear assembly 40 is selectively configurable to cooperate with one or more oscillation components 46 that may be selectively adjusted to vary the oscillation angle of the swing gear 48 as explained in more detail below with respect to FIG. 4D. More particularly, the housing 20 includes an angular displacement mechanism or lock 80 that is configured to selectively lock the motor 50 at one of a series of angular positions as denoted by indicia 82a-82c disposed thereon. Actuation of the lock 80 (e.g., pressing lock 80 into housing 20 in the direction "P") causes lock 80 to rotate about pivot 81 freeing the user to rotate the orientation of the motor 50 relative to housing 20 and gear assembly 40. As explained in more detail with respect to FIGS. 4A-4D, rotation of the motor 50 in the direction "A" reorientates the input shaft 41 and shaft 42 relative to the gear assembly 40 causing the gear assembly 40 to correspondingly rotate the swing angle of the swing gear 48 which, in turn, corresponds to the oscillation angle of the surgical tool 100 (e.g., drill bit). In embodiments, the swing angle of the swing gear relative to the oscillation angle may be a 1:1 ratio or a greater ratio depending upon a particular purpose. In embodiments, the ratio may be about 1:2. In other embodiments, the ratio may be about 1:3.5.

As mentioned above, a proximal end 25a of the tool shaft 25 is configured to selectively engage a collet 35 disposed within the housing 20 and operably associated with a locking collar 70. Locking collar 70 is rotatable between an open position which orients the collet 35 for selective receipt of the proximal end 25a of the tool shaft 25 and a locked position that engages the collet 35 onto the proximal end 25a of tool shaft 25. In embodiments, the proximal end 25a of the tool shaft 25 is keyed to facilitate engagement with the collet 35. The user simply rotates the locking collar 70 opposite the arrow "L" to load a tool shaft 25 and surgical tool thereon and then rotates the locking collar 70 in the reverse direction "L" to lockingly engage the tool shaft 25 within the collet 35. Collet 35 includes driveshaft 37 disposed on a proximal end thereof that is configured to mesh with the swing gear 48 such that oscillation of the swing gear 48 correspondingly oscillates the driveshaft 37, which, in turn, oscillates the tool shaft 25 when engaged.

Figure 4A:
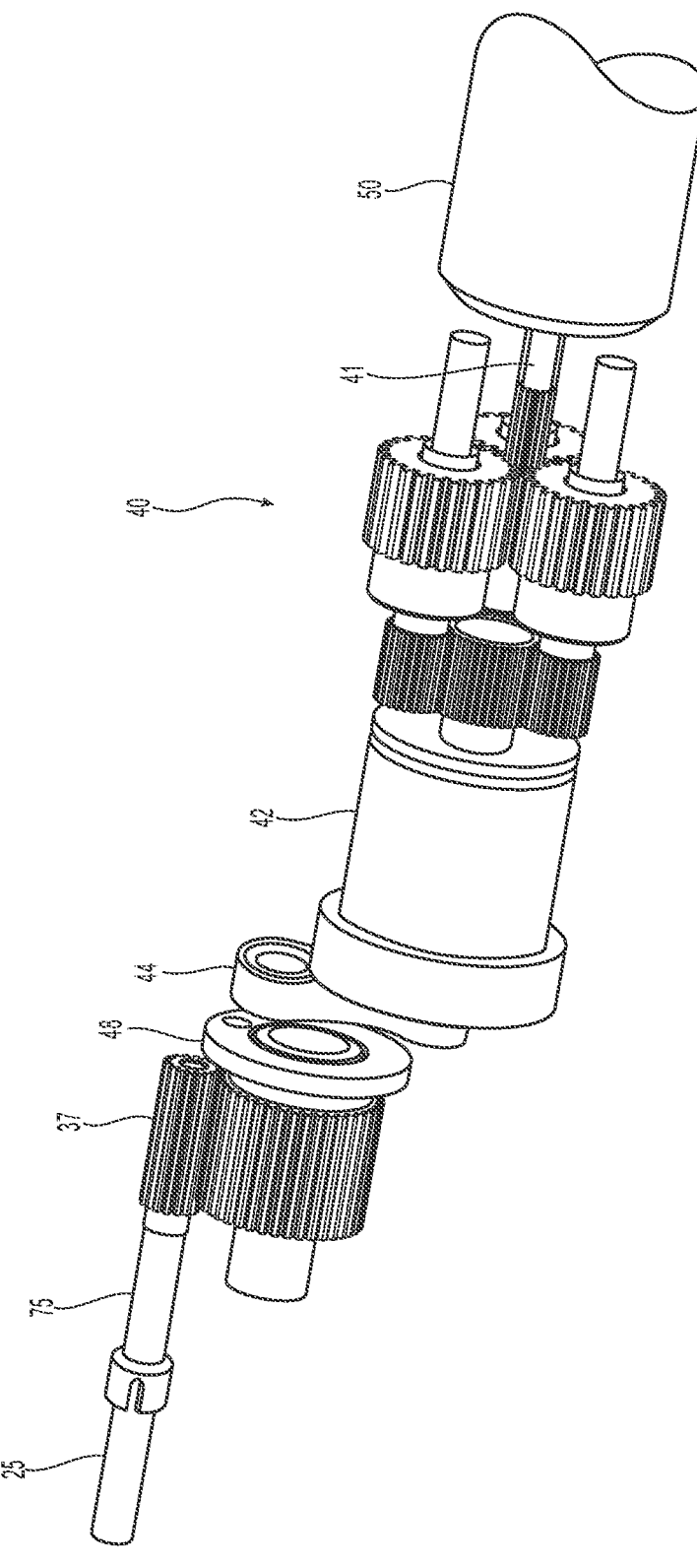
FIG. 4A is a rear, perspective view of a gear assembly and a motor of the cutting and shaving surgical device of FIG. 1.
Figure 4C:
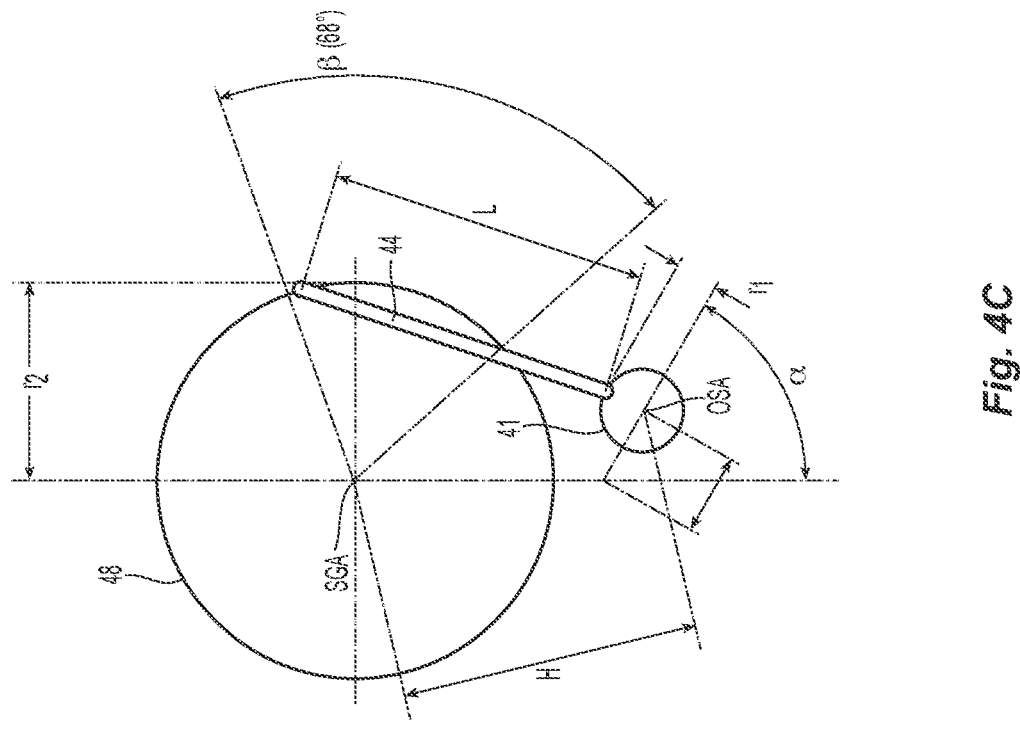
FIGS. 4B-4C are schematic views of a 4-Bar linkage diagram showing the angular displacement of the swing gear for two different gear configurations.
Figure 4B:
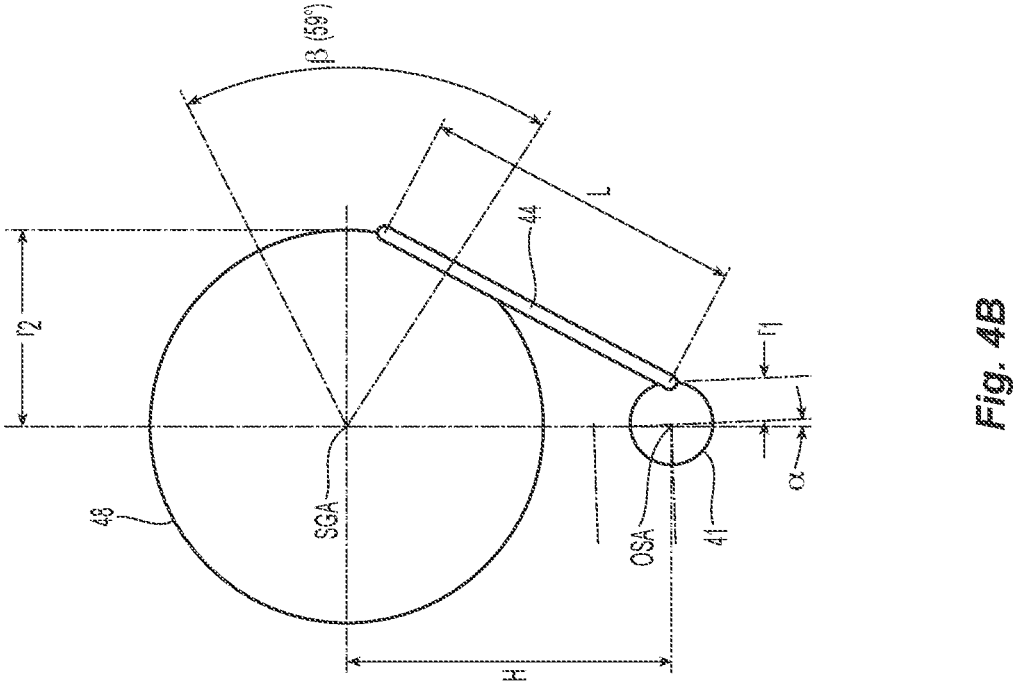
Figure 4D:
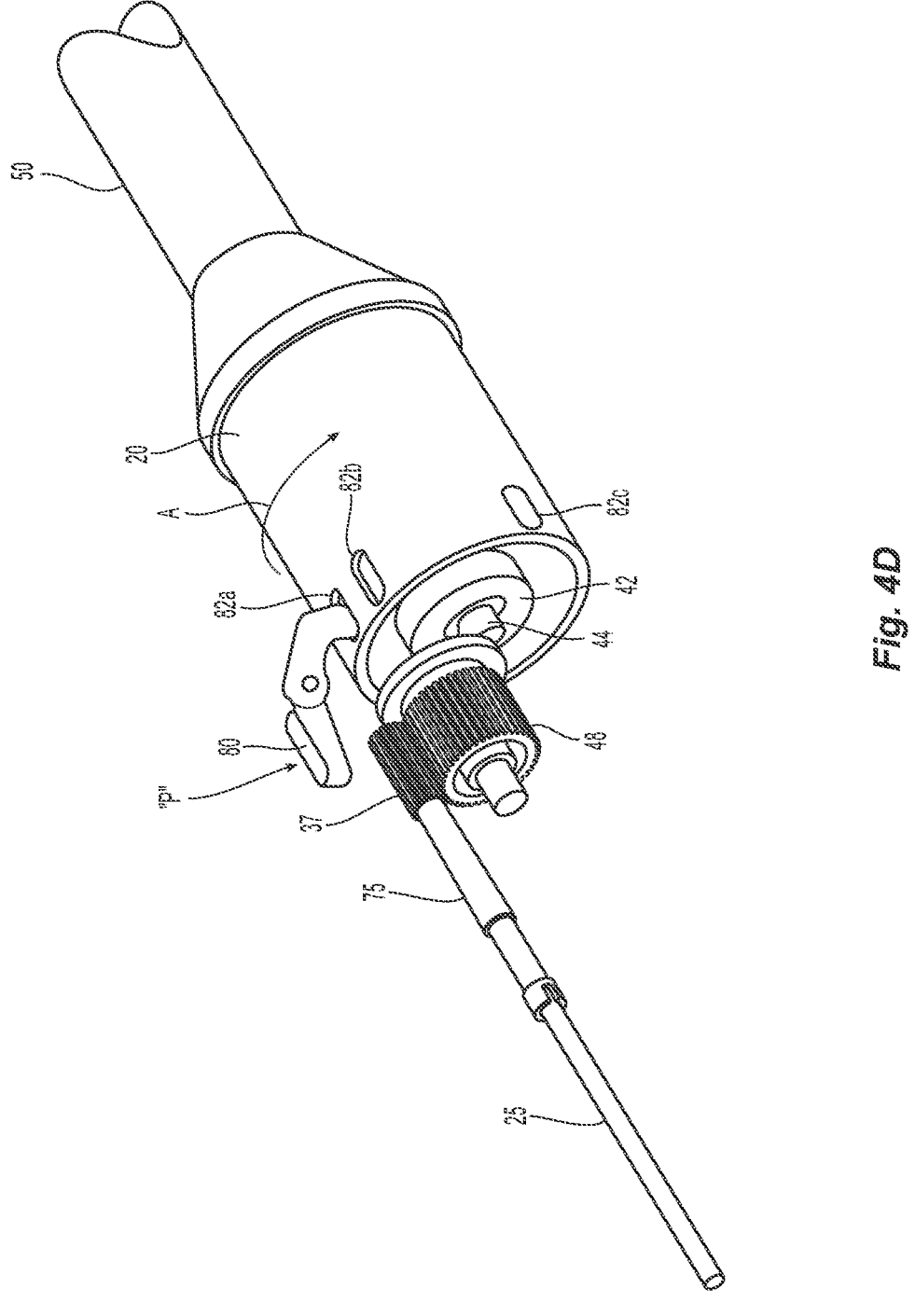
FIG. 4D is a front, perspective view of a gear housing moveable and lockable relative to the motor via an angular displacement locking mechanism.

Turning to FIGS. 4A-4D, FIG. 4A shows a rear perspective view of the input shaft 41 connected to the gear assembly 40 and the output shaft 42 and how the link 44 oscillates the swing gear 48 which, in turn, oscillates the tool shaft 25. FIG. 4B is a schematic representation of the mechanics behind the 4-Bar linkage assembly of the swing gear 48 and the angular travel of the swing gear 48 and relation of travel or angular displacement of the swing gear 48 as it relates to the position of the gear assembly housing 20. More particularly, and as mentioned above, the gear assembly housing 20 includes angular displacement lock 80 that is configured to selectively lock the motor 50 at one of a series of angular positions as denoted by indicia 82a-82c disposed thereon.

Oscillation of the swing gear 48 is based on the following factors as shown in FIG. 4B: the distance "H" between the swing gear axis SGA and the output shaft axis OSA; "L"—the link 44 length; "r1"—the distance from the link 44 connection to the center of the output shaft axis OSA; and "r2"—the distance from the link 44 connection to the center of the swing gear axis SGA.

Actuation of the lock 80 (e.g., pressing lock 80 into housing 20 in the direction "P") causes lock 80 to rotate about pivot 81 freeing the user to rotate the orientation of the motor 50 relative to gear assembly housing 20 and gear assembly 40. As shown in FIG. 4B this moves the center of the output shaft axis OSA and distance "H" effecting the angular displacement of the swing gear 48 as shown.

By comparison and, for example, FIG. 4B shows gear housing 20 with the lock 80 in position 82c wherein the swing gear 48 is at a minimum angular displacement (59°) and the motor output shaft axis OSA is in general registry with the swing gear axis SGA. Moreover, the distance "H" is at a maximum. When the user rotates the motor 50 to increase the angular displacement, for example to position 82b, the angular displacement of the motor output shaft axis OSA moves away from the swing gear axis SGA and the angle α gets greater (See FIG. 4C) coupled with the distance from the swing gear axis SGA to the output gear axis "H" getting smaller (See FIG. 4C). As a result, the swing gear total angular travel β increases (68°). In position 82a, the motor 50 is rotated to a maximum angularly displaced orientation and the swing gear 48 is oscillating at a maximum angle. As mentioned herein, this allows the surgical tool 100 to cut more aggressively as explained in more detail below.

Housing 20 also supports a tool exposure mechanism 30 that is configured to regulate the length of exposure of the surgical tool 100 relative to the distal end 16 of the elongated tube 12. This provides the surgeon with additional flexibility when using the surgical device 10. More particularly and as best shown in FIG. 2, collet 35 is selectively moveable within a cavity 39 defined in housing 20. Rotation of the tool exposure mechanism 30 in a counter-clockwise direction "R1" correspondingly moves the collet 35 within the cavity 39 a distance of "E1". Movement of the collet 35 in a direction "E1", in turn, exposes the surgical tool 100 a corresponding distance "E2" from the distal end 16 of the elongated tub 12. In embodiments, "E1" and "E2" may be equivalent or in other embodiments, "E1" and "E2" may be different and movable subject to a specific gear ratio. Rotation of the tool exposure mechanism 30 in the opposite direction will retract the surgical tool 100 within the distal end 16. In embodiments, other types of actuators are contemplated, e.g., a slide actuator, a toggle, etc. In embodiments, the elongated tube may be configured to slide relative to the driveshaft to regulate tool exposure.

In use, a surgeon initially loads a surgical tool 100 drive shaft 25 into the housing 20 of device 10 by rotating lock 70 in a counter-clockwise direction (opposite direction of "L") to open collet 35. Once open, the surgeon slides the shaft 25 within elongated tube 12 such that the proximal end 25a of the shaft 25 bottoms out into the collet 35 or otherwise engages the collet 35. The surgeon then rotates the lock 70 in the opposite direction "L" to close the collet 35 onto the proximal end 25a and lock the tool shaft 25 within device 10. Once locked, the device 10 is ready for use.

If a surgeon wants to change the angular displacement of the oscillation of the surgical tool 100 for a particular surgical purpose, e.g., adjust the aggressiveness (finer cutting or more aggressive cutting) of the surgical tool 100, the surgeon simply depresses the angular displacement lock 80 and rotates the motor 50 relative to the housing 20. As mentioned above, rotation of the motor 50 correspondingly adjusts one or more gears of the gear assembly 40 which, in turn, adjusts the swing angle of the swing gear 48 effecting the angle of oscillation of the surgical tool 100.

Additionally, if a surgeon wants to change the exposure length "E2" of surgical tool 100 for a particular surgical purpose, e.g., better control, visibility or depth of plunge, the surgeon simply rotates the tool exposure mechanism 30 to move collet 35 which, in turn, extends or retracts the exposure length "E2" of the surgical tool 100 relative to the distal end 16 of the elongated tube 12.

Figures 5A, 5B, 5C:
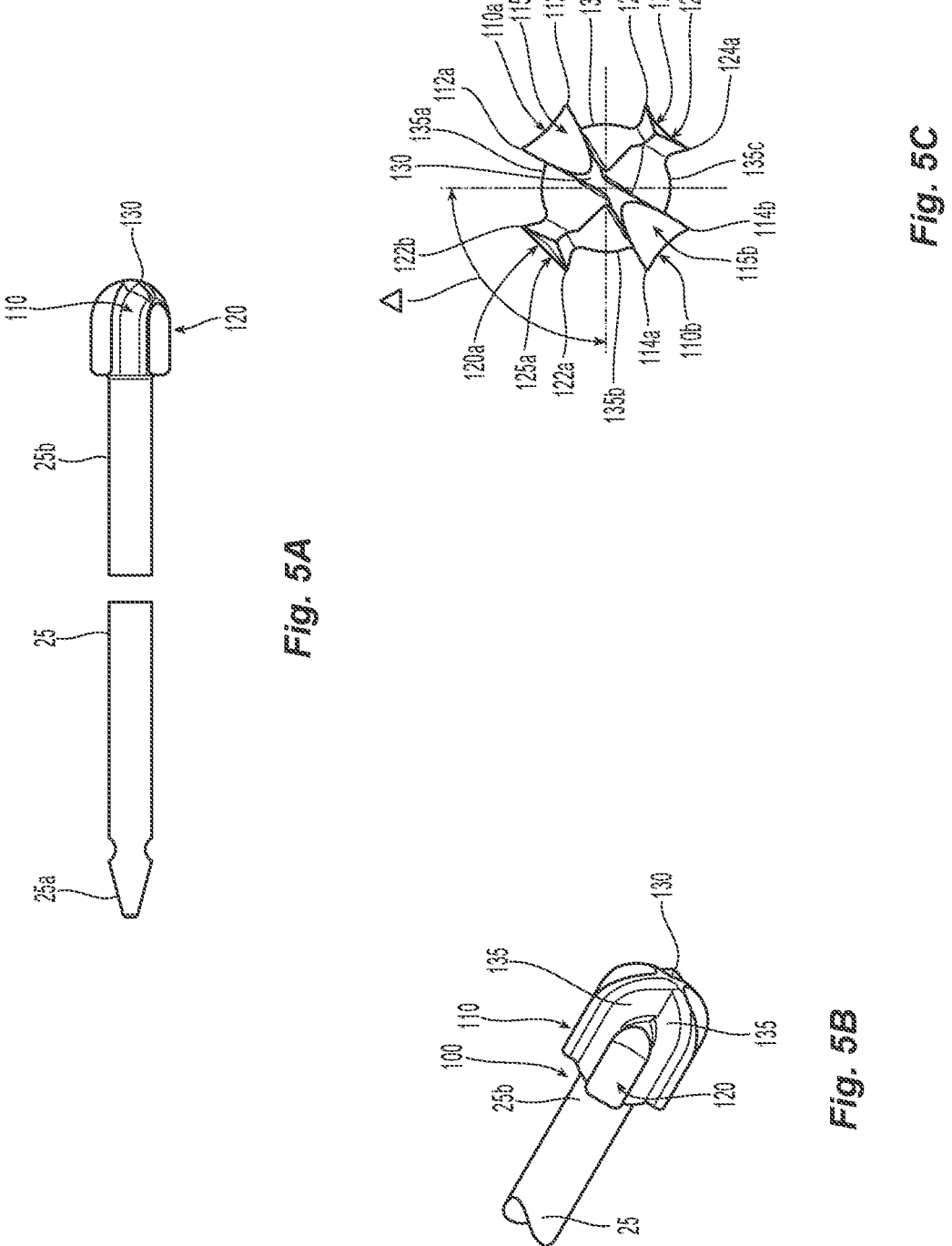
FIGS. 5A-5C are various enlarged views of a surgical tool for use with embodiments of the cutting and shaving surgical devices described herein.

Turning to FIGS. 5A-5C which show various views of the surgical tool 100, which, in this particular case, is shown a drill bit that may be used for both plunge-cutting into bone or hard tissue and shaving. More particularly, surgical tool 100 (hereinafter "drill bit 100") is disposed at the distal end 25b of the drive shaft 25 and includes a series of cutting flutes disposed therearound, generally identified as flutes 110 and 120, as well as a cutting tip 130 at a distal-most end thereof. Generally, cutting tip 130 facilitates plunge-cutting into bone or hard tissue while flutes 110 and 120 facilitate shaving. However, the flutes 110 and 120 and cutting tip 130 may each be configured to facilitate both cutting and shaving depending upon a particular purpose.

Drill bit 100 includes two pairs of opposing flutes, namely, flutes 110a, 110b and flutes 120a, 120b. Any number of cutting flutes may be employed, but for the purposes herein, flutes are described as a pair of flutes 110a, 110b. Flutes 110a, 110b are generally larger than flutes 120a, 120b and converge to form cutting tip 130 at a distal end thereof. Flute 110a includes a deep groove 115a defined between opposing cutting edges 112a, 112b which, when the drill bit 100 is oscillating, facilitates removal of the bone fragments. Flute 110b includes similar elements on the opposing side of the drill bit 100, namely, groove 115b defined between cutting edges 114a, 114b. Flutes 110a, 110b and the cutting tip 130 cooperate to facilitate plunge-cutting into bone or hard tissue. The cutting edges 112a, 112b and 114a, 114b of flutes 110a, 110b are also configured to cooperate with flutes 120a, 120b to facilitate shaving or side cutting.

Flutes 120a includes a deep groove 125a defined between opposing cutting edges 122a, 122b which, when the drill bit 100 is oscillating, facilitates removal of the bone fragments when shaving. Flute 120b includes similar elements on the opposing side of the drill bit 100, namely, groove 125b defined between cutting edges 124a, 124b. Sections 135a-135d are defined between adjacent flutes, e.g., section 135a is defined between flute 110a and flute 120a and are configured to facilitate removal as well. Sections 135a-135d are also configured to facilitate the removal of bone or tissue during both plunge-cutting and shaving.

In contrast to rotational cutting which generally requires a single leading cutting edge to cut bone as the rotational cutting tool rotates in a single direction, the drill bit 100 of the present disclosure includes two edges on opposite sides of the groove 115a which provide a leading cutting edge during clockwise rotation, e.g., cutting edge 112b, and a leading cutting edge during counter-clockwise rotation, e.g., cutting edge 112a. This enhances plunge-cutting with the larger flutes 110, 110b. Similarly, flutes 120a, 120b each include opposing cutting edges, e.g., edges 114a, 114b, which act as leading edges for bone and tissue shaving.

By adjusting the oscillation angle via actuating the angular adjust lock 80 and rotating the motor 50, a surgeon can opt for a greater oscillation angle Δ for more aggressive cutting or a lower oscillation angle Δ for finer cutting. In embodiments, the drill bit 100 may be keyed (or configured to allow insertion in only one orientation). Changing the drill bit 100 oscillation angle Δ without changing the speed of the motor 50 will alter the cutting performance of the drill bit 100. For example, if the oscillation angle Δ is increased the drill bit 100 will rotationally travel faster and further which increases the number of flutes cutting bone. Likewise, if the oscillation angle Δ is decreased, the drill bit 100 will rotationally travel slower and less radial distance which reduces the number of flutes cutting bone.

While several aspects of the disclosure have been shown in the drawings, it is not intended that the disclosure be limited thereto, as it is intended that the disclosure be as broad in scope as the art will allow and that the specification be read likewise. For example, it is contemplated that the instead of rotating the motor 50 to adjust the oscillation angle Δ, the motor 50 may be fixed and the swing gear 48 may be location may be selectively moveable to adjust the oscillation angle Δ. Therefore, the above description should not be construed as limiting, but merely as exemplifications of particular configurations. Those skilled in the art will envision other modifications within the scope and spirit of the claims appended hereto.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended hereto.

What is claimed is:

1. A surgical device for cutting or shaving bone or hard tissue, comprising:
  a housing including an elongated tube extending therefrom, the elongated tube configured to support a surgical tool at a distal end thereof;
  a gear assembly disposed within the housing and configured to control oscillation of the surgical tool; and
  a motor operably coupled to the housing and configured to drive the gear assembly upon activation thereof, the motor or at least one gear of the gear assembly moveable relative to the housing to adjust an oscillation angle of the surgical tool.

2. The surgical device for cutting or shaving tissue according to claim 1, wherein the motor is operably coupled to the housing and configured to drive the gear assembly upon activation thereof, the motor moveable relative to the housing to adjust at least one gear of the gear assembly which, in turn, adjusts the oscillation angle of the surgical tool.

3. The surgical device for cutting or shaving tissue according to claim 1, wherein the motor is rotatable relative to the housing to adjust the at least one gear of the gear assembly.

4. The surgical device for cutting or shaving tissue according to claim 3, wherein the housing includes an angular displacement mechanism which, upon actuation, is configured to allow selective rotation of the motor relative to the housing.

5. The surgical device for cutting or shaving tissue according to claim 1, wherein movement of the motor relative to the housing effects an oscillation angle of a swing gear of the gear assembly which, in turn, effects the oscillation angle of the surgical tool.

6. The surgical device for cutting or shaving tissue according to claim 1, wherein the surgical tool includes a drive rod that is selectively engageable within the housing.

7. The surgical device for cutting or shaving tissue according to claim 6, wherein the drive rod of the surgical tool is selectively engageable with a collet disposed within the housing and wherein the collet is operably engageable with the gear assembly.

8. The surgical device for cutting or shaving tissue according to claim 7, wherein the collet cooperates with a lock collar to selectively lock the drive rod of the surgical tool therein.

9. The surgical device for cutting or shaving tissue according to claim 1, wherein the surgical tool is a drill bit configured to cut or shave bone or tissue upon activation thereof.

10. The surgical device for cutting or shaving tissue according to claim 9, wherein the drill bit is configured to both plunge-cut into bone or tissue and side cut to shave bone or tissue.

11. A surgical device for cutting or shaving bone or hard tissue, comprising:
  a housing including an elongated tube extending therefrom, the elongated tube configured to support a surgical tool at a distal end thereof, the surgical tool including a drive rod selectively engageable within the housing;
  a gear assembly disposed within the housing and configured to control oscillation of the surgical tool;
  a motor operably coupled to the housing and configured to drive the gear assembly upon activation thereof, and
  a collet disposed within the housing and configured to selectively lock the drive rod of the surgical tool within the housing, the collet operably engageable with the gear assembly such that actuation of the motor oscillates the surgical tool,
  wherein the motor is rotatable relative to the housing to adjust at least one gear of the gear assembly which, in turn, adjusts an oscillation angle of the surgical tool.

12. The surgical device for cutting or shaving tissue according to claim 11, further comprising an angular displacement mechanism operably associated with the housing which, upon actuation, is configured to allow selective rotation of the motor relative to the housing.

13. The surgical device for cutting or shaving tissue according to claim 11, wherein rotation of the motor relative to the housing effects an oscillation angle of a swing gear of the gear assembly which, in turn, effects the oscillation angle of the surgical tool.

14. The surgical device for cutting or shaving tissue according to claim 11, wherein the collet is selectively moveable within the housing to control a length of exposure of a tip of the surgical tool relative to a distal end of the elongated tube.

15. The surgical device for cutting or shaving tissue according to claim 14, further comprising a dial disposed on the housing, the dial rotatable relative to the housing to control the length of exposure of the tip of the surgical tool relative to the distal end of the elongated tube.

16. A surgical device for cutting or shaving bone or hard tissue, comprising:
  a housing including an elongated tube extending therefrom, the elongated tube configured to support a surgical tool at a distal end thereof, the surgical tool including a drive rod selectively engageable within the housing;
  a gear assembly disposed within the housing and configured to control oscillation of the surgical tool;
  a motor operably coupled to the housing and configured to drive the gear assembly upon activation thereof, the motor moveable relative to the housing to adjust at least one gear of the gear assembly which, in turn, adjusts an oscillation angle of the surgical tool; and
  a collet disposed within the housing and configured to selectively lock the drive rod of the surgical tool within the housing, the collet operably engageable with the gear assembly such that actuation of the motor oscillates the surgical tool, wherein the collet is selectively moveable within the housing to control a length of exposure of a tip of the surgical tool relative to a distal end of the elongated tube.

17. The surgical device for cutting or shaving tissue according to claim 16, wherein the housing includes an angular displacement mechanism which, upon actuation, is configured to allow selective rotation of the motor relative to the housing.

18. The surgical device for cutting or shaving tissue according to claim 16, wherein movement of the motor relative to the housing effects an oscillation angle of a swing gear of the gear assembly which, in turn, effects the oscillation angle of the surgical tool.

19. The surgical device for cutting or shaving tissue according to claim 18, wherein movement of the motor relative to the housing moves an axis of rotation of the motor relative to an axis of rotation of the swing gear which effects the movement of a corresponding link operably connected to the swing gear which, in turn, effects the oscillation angle of the swing gear and the oscillation angle of the surgical tool.

20. A surgical device for cutting or shaving bone or hard tissue, comprising:

a housing including an elongated tube extending therefrom, the elongated tube configured to support a surgical tool at a distal end thereof, the surgical tool including a drive rod selectively engageable within the housing;

a gear assembly disposed within the housing and configured to control oscillation of the surgical tool;

a motor operably coupled to the housing and configured to drive the gear assembly upon activation thereof, a collet disposed within the housing and configured to selectively lock the drive rod of the surgical tool within the housing, the collet operably engageable with the gear assembly such that actuation of the motor oscillates the surgical tool; and an angular displacement mechanism operably associated with the housing which, upon actuation, is configured to allow selective rotation of the motor relative to the housing.

\*　\*　\*　\*　\*